(12) United States Patent
Methling

(10) Patent No.: US 10,494,572 B2
(45) Date of Patent: Dec. 3, 2019

(54) METHOD FOR THE DEGRADING OF SYNTHETIC POLYMERS AND DEVICE FOR CARRYING OUT SAID METHOD

(71) Applicant: Achim Methling Joesef Ranftl GbR, Furstenfeldbruck (DE)

(72) Inventor: Achim Methling, Vienna (AT)

(73) Assignee: Achim Methling Joesef Ranftl GbR, Furstenfeldbruck (DE)

( * ) Notice: Subject to any disclaimer, the term of this patent is extended or adjusted under 35 U.S.C. 154(b) by 426 days.

(21) Appl. No.: 14/782,489

(22) PCT Filed: Mar. 27, 2014

(86) PCT No.: PCT/EP2014/056166
§ 371 (c)(1),
(2) Date: Oct. 5, 2015

(87) PCT Pub. No.: WO2014/161767
PCT Pub. Date: Oct. 9, 2014

(65) Prior Publication Data
US 2016/0040074 A1 Feb. 11, 2016

(30) Foreign Application Priority Data
Apr. 4, 2013 (DE) .......................... 10 2013 205 996

(51) Int. Cl.
*C10G 1/10* (2006.01)
*C07C 4/22* (2006.01)
(Continued)

(52) U.S. Cl.
CPC ............ *C10G 1/10* (2013.01); *B01J 19/0013* (2013.01); *B01J 19/1862* (2013.01); *C07C 4/22* (2013.01); *C08J 11/12* (2013.01); *C10G 1/002* (2013.01); *B01J 2219/00006* (2013.01); *B01J 2219/00063* (2013.01); *B01J 2219/00087* (2013.01); *B01J 2219/00159* (2013.01); *B01J 2219/00162* (2013.01); *B01J 2219/00166* (2013.01); *B01J 2219/00168* (2013.01); *B01J 2219/00184* (2013.01); *B01J 2219/24* (2013.01); *C08J 2323/02* (2013.01); *C08J 2323/08* (2013.01);
(Continued)

(58) Field of Classification Search
CPC ..................................... C07C 4/22; C10G 1/10
USPC ...................................... 422/184.1, 198, 649
See application file for complete search history.

(56) References Cited

U.S. PATENT DOCUMENTS 4,096,069 A * 6/1978 Postavnichev ......... B01D 35/12
210/342
4,584,421 A 4/1986 Saito et al.
(Continued)

FOREIGN PATENT DOCUMENTS

DE 19722586 A1 12/1998
EP 0276081 A2 7/1988
(Continued)

OTHER PUBLICATIONS

JPH09268293 (machine translation of Japanese patent JPH09268292; (1997)) (Year: 1997).*

*Primary Examiner* — Philip Y Louie
(74) *Attorney, Agent, or Firm* — The Webb Law Firm

(57) ABSTRACT

A method for breaking down synthetic polymers, in particular polyolefins, is provided. In addition a system for carrying out said method and a product according to said method is provided.

13 Claims, 6 Drawing Sheets

(51) Int. Cl.
*C08J 11/12* (2006.01)
*C10G 1/00* (2006.01)
*B01J 19/00* (2006.01)
*B01J 19/18* (2006.01)

(52) U.S. Cl.
CPC ......... *C08J 2323/10* (2013.01); *Y02W 30/703* (2015.05)

(56) References Cited

U.S. PATENT DOCUMENTS

| | | | | |
|---|---|---|---|---|
| 4,851,601 A | * | 7/1989 | Fukuda | C10G 1/002 |
| | | | | 208/120.01 |
| 5,386,055 A | * | 1/1995 | Lee | B01J 3/008 |
| | | | | 210/180 |
| 2003/0199718 A1 | * | 10/2003 | Miller | C10G 1/00 |
| | | | | 585/241 |
| 2006/0205900 A1 | * | 9/2006 | Windmuller | C08F 210/18 |
| | | | | 526/160 |
| 2007/0179326 A1 | | 8/2007 | Baker | |
| 2008/0179257 A1 | * | 7/2008 | Clarke | B09B 3/00 |
| | | | | 210/741 |
| 2009/0036725 A1 | * | 2/2009 | Wu | C08F 10/00 |
| | | | | 585/521 |
| 2009/0117015 A1 | * | 5/2009 | Shimo | C08J 11/12 |
| | | | | 422/184.1 |
| 2009/0264693 A1 | * | 10/2009 | Xie | B01J 29/7615 |
| | | | | 585/650 |
| 2010/0324347 A1 | | 12/2010 | Kelkar et al. | |

FOREIGN PATENT DOCUMENTS

| | | | |
|---|---|---|---|
| EP | 1212387 B1 | 2/2006 | |
| EP | 2161299 A1 | 3/2010 | |
| EP | 1745115 B1 | 12/2010 | |
| FR | 2931482 A1 | 11/2009 | |
| JP | 63178195 A | 7/1988 | |
| JP | 386790 A | 4/1991 | |
| JP | 776688 A | 3/1995 | |
| JP | 7205147 A | 8/1995 | |
| JP | 9268293 A | 10/1997 | |
| JP | 9279157 A | 10/1997 | |
| JP | 2007529574 A | 10/2007 | |
| JP | 2012530810 A | 12/2012 | |
| WO | 0066656 A1 | 11/2000 | |
| WO | WO-2005094990 A1 * | 10/2005 | ............ B01J 29/08 |
| WO | WO 2005094990 A1 * | 10/2005 | ............ B01J 29/08 |

* cited by examiner

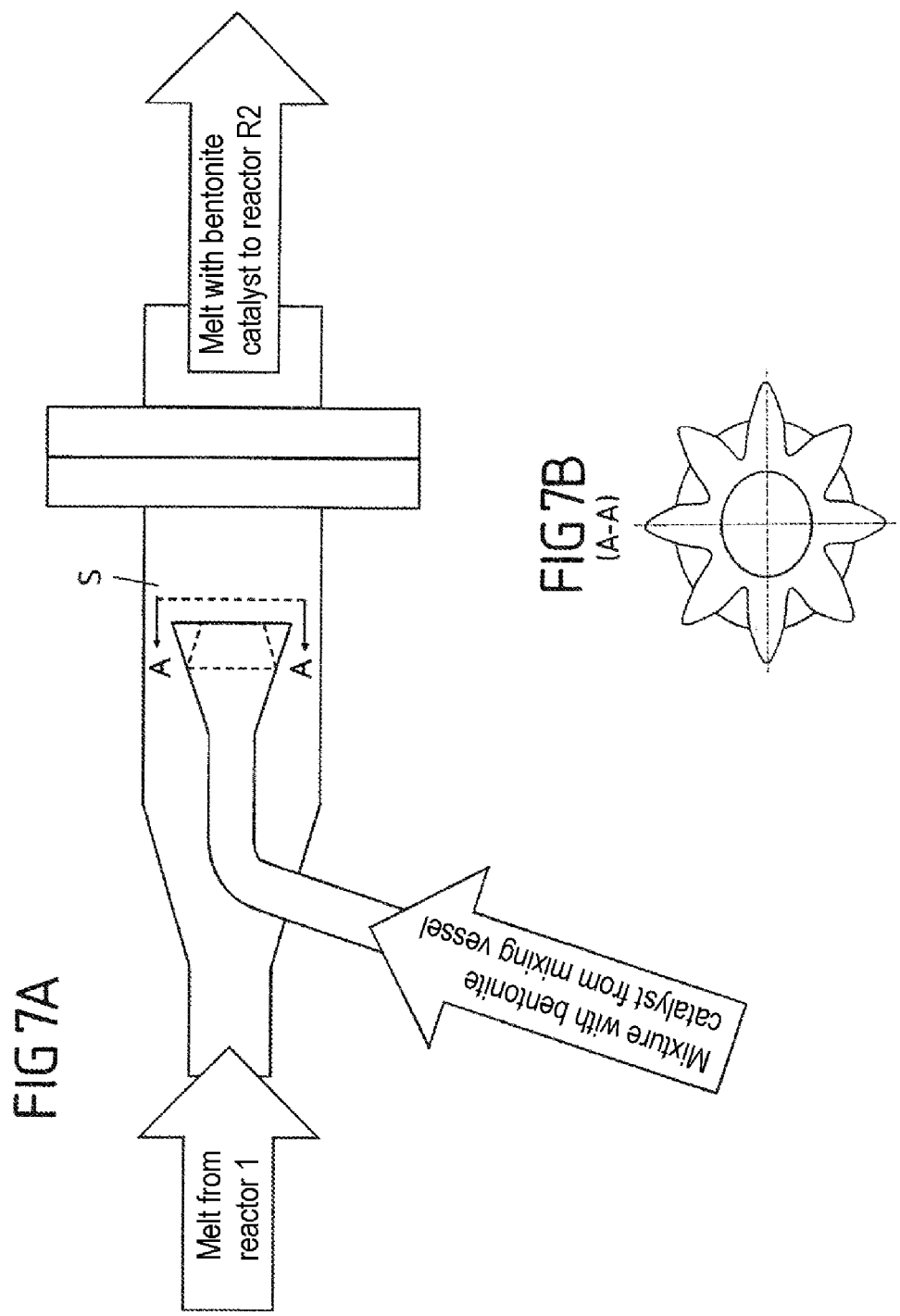

METHOD FOR THE DEGRADING OF SYNTHETIC POLYMERS AND DEVICE FOR CARRYING OUT SAID METHOD

CROSS-REFERENCE TO RELATED APPLICATIONS

This application is the United States national phase of International Application No. PCT/EP2014/056166 filed Mar. 27, 2014, and claims priority to German Patent Application No. 10 2013 205 996.5 filed Apr. 4, 2013, the disclosures of which are hereby incorporated in their entirety by reference.

BACKGROUND OF THE INVENTION

Field of the Invention

The present invention relates to a method for breaking down synthetic polymers, in particular polyolefins, to a device and/or a system for carrying out said method and to a product oil that is produced using the method.

Description of Related Art

It is no longer possible to imagine our modern world without plastics based on synthetic polymers, such as polyolefins, for example. Polyolefins such as polyethylene (PE) or polypropylene (PP) are used on a large scale as packaging materials in the consumer goods industry. Although great efforts for reutilization or recycling of such plastics are being undertaken, there is still a requirement for efficient utilization or reuse of the polyolefins processed in the packaging materials.

For instance, in the countries of the European Union, Norway and Switzerland, for example, 51.3% (12.8 Mt) of the end consumer plastic waste generated in 2008 was recycled, and the remaining amount (12.1 Mt) was for the most part disposed of in landfill sites or to a lesser extent fed to combustion systems without energy production. The recovered plastic waste was either fed to energy production (7.4 Mt or 30% of the end consumer plastic waste or to recycling (5.3 Mt or 21.3% of the end consumer plastic waste). Energy production in refuse incineration systems reached 6.8 megatons of plastic waste (this corresponds to 27.3% of the end consumer waste). Energy production by incineration of plastic refuse in refuse incineration systems is also termed end-of-life use. The primary concern here is disposal.

Between the years 2006 and 2008, the fraction of the reuse of plastic waste increased overall, wherein the fraction of recycling increased more greatly than the fraction for energy production. The fraction of energy production and recycling of plastic waste differs greatly between the European countries. Thus, in Norway, Sweden, Germany, Denmark, Belgium and Switzerland, energy production rates were achieved of between 85% and 99.5%. This is due, in particular, to the extensive restrictions on disposal of plastic waste in landfill in these countries.

As mentioned, a large fraction of the plastic waste is not only fed to refuse incineration systems for the purpose of energy use, but also recycled. The recycling rate depends greatly on the various types of plastic. For instance, 40% of the bottles and industrial films and over 90% of crates and boxes are recycled. Less than 10% of the remaining mixed plastics, in contrast are recycled in the EU. The overall recycling rate of packaging materials domestically and commercially was 29% in 2008 in the EU, and the reuse rate was estimated at approximately 58%.

In the recycling plants for polymeric plastics, the scrap plastics which contain at least 92% polymer plastics are supplied in bale form. These bales pass through the working steps of bale opening, shredding, separating off metallic/mineral constituents, separating off biogenic substances, separating off lignin-containing substances, separating off chlorinated plastics, washing, drying and separation into polyethylene fractions and polypropylene fractions. The pure polyethylene fractions and the pure polypropylene fractions are processed at qualified recycling enterprises to give regrind materials and are then fed back to the industrial cycle. The scrap plastic waste which are not separable into segregated materials and which do not suit recycled material processes, but nevertheless have a polyolefin content of greater than 90%, are currently not reused at all, or only inadequately.

A general problem in the reuse of plastic waste is the composition of the plastics used. For instance, the plastics products used in the consumer sector such as, for example, bottles, typically consist of various polyethylenes such as, for example, hard polyethylene (HDPE), or polyethylene terephthalate (PET), wherein the plastic waste consisting of pure polymers are already recycled and reused to a great extent.

In contrast, recycling plastic waste which consist of mixtures of different polymers is a problem, as is the case, for example, with polyethylene or polypropylene. LDEP (low density polyethylene), HDPE (high density polyethylene) and PP (polypropylene) form about half of the global plastic waste.

Even if the reuse of plastic waste in the form of recycling, or combustion for energy production, has increased in recent years, there is still a demand for improved methods for utilizing plastic waste, in particular since the worldwide consumption has increased enormously owing to emerging countries. Also, a rational reuse of plastic waste is necessary, since the starting materials made from petroleum or natural gas that are usually used for producing plastics are limited.

Thus, various approaches have already been described in the past for breaking down or converting plastic waste into the hydrocarbons underlying the plastics.

For instance, U.S. Pat. No. 4,584,421 discloses a method in which plastics or shredded plastics are subjected to a thermal decomposition or thermal breakdown in the presence of a suitable catalyst such as, for example, a zeolite catalyst, and in this case are converted into liquid hydrocarbon oil. In this method, the shredded plastics are first melted and then thermally broken down at a temperature between 440° and 470° C., and the gaseous products of the thermal breakdown are introduced into a catalyst bed at temperatures between 350° and 470° Celsius. In this case a second thermal decomposition proceeds and the production of an oil consisting of lower hydrocarbons, in particular $C_5$ to $C_{29}$ hydrocarbons takes place. The molecular weight of the lower hydrocarbons produced from the shredded plastics is in a range between 135 and 190.

EP 1745115 B1 discloses a further method and a device for obtaining fractionated hydrocarbons from plastics materials. In the method described here, first a compacted mass of plastic waste, in particular polypropylene, polyethylene and polystyrene plastics of hard and soft plastics fractions are heated up in a melt container, wherein a first liquid phase and a first gas phase form. The liquid phase and the first gas phase are then transported into a vaporization vessel in which they are further warmed, developing a second liquid phase and a second gas phase. The second liquid phase is in turn transferred to a reheater and there further heated with further heat introduction in such a manner that formation of a third gas phase occurs. The second gas phase from the vaporization container and the third gas phase from the reheater are transferred to a cracking tower, in which further breakup (cracking) of the long-chain hydrocarbons into short-chain hydrocarbons takes place. The yield of product oil formed from the plastic waste is between 75 and 90%, wherein said yield is dependent on the plastics varieties introduced.

DE 197 22 586 A1 discloses a further method which describes a method and equipment for obtaining paraffins and/or microwaxes from waste plastics. This method serves exclusively for production of paraffins and/or microwaxes.

The currently known methods for breakdown of synthetic polymers from plastic waste, however, are not optimal in relation to usability or applicability of the product oil produced and are in need of improvement. A processing of non-presorted, purified and pre-agglomerated waste plastics is currently not controllable, or only controllable with great difficulty with respect to processing in industrial plants. Achieving clearly defined, pure and readily applicable end products from non-preprocessed waste plastics, in addition, has not yet been successful industrially.

SUMMARY OF THE INVENTION

It is therefore an object of the present invention to provide a method for the breakdown of plastic waste with an increased efficiency and product yield, in particular with improved usability of the product oils produced.

Correspondingly, a method is provided for breaking down synthetic polymers, in particular polyolefins, as may be found, for example in plastic waste, which comprises the following steps:
a) producing a melt of synthetic polymers, in particular of dry synthetic polymers,
b) purifying the polymer melt by passing the polymer melt through at least one melt filter,
c) transferring the purified polymer melt into at least one first reactor, wherein the purified polymer melt in the at least one first reactor is conducted from a lower region to an upper region of the reactor with heating to temperatures between 300° C. and 370° C., preferably 340° C. to 360° C., particularly preferably 350° C., wherein the polymers in the at least one first reactor are cleaved into oligomers,
d) transferring the oligomer mixture formed in the at least one first reactor to at least one second reactor, wherein the oligomer mixture in the at least one second reactor is conducted from a lower region to an upper region of the reactor with heating to temperatures between 380° C. and 450° Celsius, preferably 400° C. to 430° C., particularly preferably 410° Celsius, wherein the oligomers in the at least one second reactor are broken down to short-chain hydrocarbons in the presence of at least one clay mineral as depolymerization catalyst,
e) removing the short-chain hydrocarbons that are formed in the at least one second reactor to at least one precondenser, wherein the short-chain hydrocarbons (C3→C22) exiting from the at least one second reactor are cooled in the at least one precondenser; and
f) introducing the short-chain hydrocarbons that are cooled in the at least one precondenser into at least one main condenser, wherein the short-chain hydrocarbons exiting from the at least one precondenser are liquefied in the at least one main condenser.

It is preferred in particular when mixtures of synthetic polymers, in particular mixtures of polyolefins, such as polyethylene (PE) and polypropylene (PP) are broken down.

Correspondingly, the present method permits the workup of unsorted end consumer plastic waste which originate in particular from non-separable mixed waste. A particular advantage of the present method is that the mixing ratio of polyethylenes and polypropylenes is unimportant in the present case. Thus all desired mixing ratios of all polyethylene types and all polypropylene types can be used; complex separation of the polyolefin waste is unnecessary.

A further advantage of the present method is that, on account of the breakdown of the polyolefins to short-chain hydrocarbons having a defined composition, energy carriers in the form of heating oils and gasoline fractions are formed and at the same time plastic waste are eliminated.

In addition, owing to the production of defined heating oil and gasoline fractions, energy is stored which can be called up on demand, for example by combustion in engine-independent vehicle heating systems or combined heat and power plants. In contrast thereto, although in the refuse incineration used for the most part the plastic waste are eliminated, this method is cost intensive and the only by-product generated is energy.

The present method generates synthetic oils (olefins) and gasoline and thereby marketable products which are in the field of gasoline fuel and heating oil. As described, the synthetic oil and gasoline products are generated in a specific manner from plastic waste fractions of the polyolefin (PE/PP) type by chemical reaction of a low-temperature pyrolysis or thermolysis proceeding under mild conditions, using an optimized residence time controller, an optimized temperature controller and an optimized control of the reactor head temperature.

The synthetic polymers or input materials used consist of more than 95% polyethylene and polypropylene mixtures. These plastic waste, in one embodiment of the present method, are first comminuted and then subjected to separation of metals, nonmetals and heavy materials. In further steps, chlorinated plastics are separated off (chlorine elimination), elimination of cellulose possibly present, washing, pressing, drying and compaction. The waste materials produced on account of the workup such as minerals, metals, fibers, paper and plastics are disposed of appropriately or biogenic waste materials can be discharged with the wash water.

The above-described treated waste plastics are then present as loose cleaned plastics shreds which are subjected to a pre-agglomeration and thereby achieve a consistency which permits introduction into the present method.

In an embodiment of the present method, the worked-up pre-agglomerated polymers are melted in an extruder, in particular in a twin-screw extruder, at temperatures up to 300° C. The prepared polymers are introduced continuously into the extruder, using a metering unit as feed appliance, wherein the metering unit used permits mass-controlled feed of the polymers into the extruder. In the metering appliance, at the same time the polymers are further dried and preheated. The feed of the prepared polymers into the extruder is controlled in this case in dependence on the polymer breakdown in the at least first and at least second reactor, for example using level measurement (e.g. in the form of a weighing appliance).

As a result of the heating and melting of the polymers proceeding in the extruder, at the same time removal of any residual moisture present in the polymers and also degassing occurs.

In a further variant of the present method, the viscosity of the polymer melt at the extruder exit is $1.5 \times 10^6$ to $2 \times 10^6$ mPas (300° C.), preferably $1.5 \times 10^6$ mPas (300° C.).

The viscosities of the polymer melt were determined via measurements of the melt flow rates by means of a rheometer, taking into account the thermal degradation at the corresponding temperatures. In general there is a linkage between the melt flow rate (MVR) and the melt viscosity $\eta^*$.

The melt viscosity $\eta^*$ is given by $$\eta^* = \frac{\tau_S}{\dot{\gamma}_S}$$

wherein $\tau_s$ is the shear stress and $\gamma_s$ is the shear rate.

The shear stress $\tau_s$ is calculated from $$\tau_S = \frac{r_D}{2 \cdot l_D} \cdot \frac{m \cdot g}{\pi \cdot r_Z^2}$$

where r=radius, d=diameter, l=length, m=load, g=acceleration due to gravity.

The shear rate is given by $$\dot{\gamma}_S = \frac{4 \cdot MVR}{\pi \cdot r_D^2}$$

where MVR=melt flow rate.

The geometry of the test instrument used is Z: cylinder (dZ=9.550 mm), D: nozzle (dD=2.095 mm, lD=8.0 mm).

The polymer melt exiting from the extruder is then transported through a heated line, preferably into a first melt pump. Subsequently, the polymer melt is conducted through the at least one melt filter in which preferably residual traces of impurities, in particular minerals, metals, fibers, are removed from the polymer melt. More preferably, at least one melt filter is arranged between the at least one exit of the extruder and at least one intake opening into the at least one first reactor. In other words, the melt filter can be provided between extruder exit and a heated tube which opens into the at least one first reactor. The at least one melt filter preferably uses a filter material in the form of a Cr/Ni-steel grid having a pore size (mesh width) between 100 and 400 μm, which is selected depending on particle size of the impurities to be removed from the polymer melt. In general, the use of filter plates (sieve plates) or filter candles, e.g. made of stainless steel, would also be possible as filter material.

The filter function of the melt filter is monitored or controlled preferably by means of a pressure sensor arranged upstream of the melt filter, which pressure sensor in turn can be connected to a central system controller.

In a further embodiment of the present method, the polymer melt exiting from the melt filter is introduced by means of a suitable melt pump into the lower region of the at least first reactor, wherein the polymer melt has a viscosity from $1.5 \times 10^6$ to $2 \times 10^6$ mPas (300° C.), preferably $1.5 \times 10^6$ mPas (300° C.) on entry into the first reactor, and here, in particular, into the lower region of the first reactor.

The melt pumps used in the present method are more preferably temperature-controlled gear wheel pumps which are heatable and maintainable at the temperature level set respectively. Also, the melt pumps preferably have a return stop, in order in this manner to prevent the return of the polymer melt into the system. The melt pumps more preferably consist of stainless steel and are preferably lubricated by the polymer melt.

The at least one first reactor which can be, for example, in the form of a stirred-tank reactor, comprises a plurality of temperature ranges, in particular a plurality of axial heating zones having at least one agitator element. In the at least one first reactor, controlled and gentle precleavage and conditioning of the polymers proceeds via control of the reaction parameters of temperature, pressure, residence time and viscosity. In addition, the first reactor is connected to a weighing appliance (it is, for example, placed on a weighing appliance or weighing cell), in such a manner that at each time point the current fill level of the first reactor can be reported to the plant controller. This permits continuous operation of the entire system and therefore a continuous method.

The agitator element used in the at least one first reactor can be present in various embodiments. For instance, it is possible to use an agitator element in the form of a spiral agitator, anchor agitator, screw or a combination thereof. Preferably, however, an agitator element is used that is a combination of spiral agitator and screw, that is to say an agitator shaft with spiral agitator and screw.

The agitator used is matched to the method. For instance, the drive is matched to the respective viscosities. The material properties are selected in such a manner that the agitator is suitable for polyolefin melts and the corresponding temperature ranges. The dimensions of the agitator are selected in adaptation to the reactors. The agitator blade combination preferably used of spiral and screw permits the generation of lift along the reactor wall and downforce in the reactor center. The agitator favors the input and distribution of the energy supplied and accelerates significantly the conversion rates.

The at least one first reactor preferably has a ratio of height:diameter (H:D) of 7:1, preferably 5.5:1. The selected reactor dimensions permit an efficient energy input, the avoidance of large temperature differences or fluctuations, and a flat temperature profile through the entire reactor.

More preferably, the purified polymer melt enters into a lower region (sump zone) of the first reactor at a temperature from 220° C. to 300° C., preferably 300° C., and on ascent in the first reactor is warmed in a temperature gradient to temperatures between 330° C. and 360° C., preferably 350° C., at the reactor head of the first reactor.

In the at least one first reactor, preferably a precleavage is performed, or a breakdown of the polymers having a typical molecular weight of $>10^5$ kg/mol into oligomers having a molecular weight between $10^2$ and $10^4$ kg/mol, preferably $10^3$ to $10^4$ kg/mol.

In a variant, the oligomer mixture leaving the upper region (head zone) of the first reactor can have a viscosity between 500 and 1500 mPas (350° C.), preferably 500 and 1000 mPas (350° C.), particularly preferably between 600 and 800 mPas (350° C.). A typical viscosity value of the oligomer mixture at the reactor head of the first reactor is 650 to 700 mPas (350° C.). The decrease in viscosity proceeding during the stepwise heating of the polymer situated in the first reactor generates a lift of the product mixture (oligomer mixture) forming along the wall of the first reactor and a simultaneous downforce in the core (what is termed loop flow or laminar melt flow). This effect can be reinforced by the agitator element.

As already mentioned, the precleavage proceeding in the at least one first reactor is controlled by the reaction parameters of temperature, pressure, residence time and viscosity.

For instance, the temperature in the upper region of the at least one first reactor is 340° C. to 360° C., preferably a maximum of 350° C. The controlled and gentle precleavage and conditioning of the polymers to form oligomers in the at least one first reactor avoids unstable operating states in the further cleavage in the following second reactor. Likewise a gentle gradual heating of the polymer melt in the first reactor prevents foaming of the polymer melt.

During the precleavage of the polymers into the corresponding oligomers in the at least one first reactor, small amounts of gaseous hydrocarbons can form which, in an embodiment, are removed via a flare and thus burnt, or, in another embodiment for energy generation, for example can be used in a gas turbine. The gaseous depolymerization products formed in the first reactor can also be introduced via a heated line into a precondenser further described hereinafter.

In a further preferred variant of the present method, the oligomer melt formed in the at least one first reactor is removed at the upper region, e.g. reactor head, of the first reactor and introduced by means of a melt pump via a pipe, preferably via a heated pipe, in a controlled manner into the at least one second reactor, in particular into the lower region (sump zone) of the second reactor.

In a preferred embodiment of the present method, the oligomer mixture leaving the at least one first reactor is mixed with the at least one clay mineral as depolymerization catalyst before it is introduced into the at least one second reactor. For this purpose, the at least one clay mineral is introduced into the oligomer melt exiting from the first reactor via a line opening into the pipe between first and second reactor. The line introducing the clay mineral preferably has a connecting piece, preferably in the form of what is termed a "Y-shaped connector". The line introducing the clay mineral ends with said connecting piece preferably in the center or core zone of the pipe between first and second reactor. As will later be explained further in detail, the at least one clay mineral is introduced into the oligomer melt leaving the first reactor in a mixture of clay mineral, paraffins and microwaxes that is produced in a separate mixing container. Preferably, 2-3% clay mineral are used per ton of plastics.

In a variant of the present method, the at least one clay mineral is selected from the group containing layer silicates, in particular montmorillonite, illite, bentonite, kaolinite, smectite, chlorite, vermiculite and mica. Also, what are termed mixed-layer minerals such as, e.g. kaolinite/smectite, chlorite/vermiculite can be used, or very frequently alternating layering of illite/smectite or illite/montmorillonite. Preferred clay minerals are bentonite and montmorillonite.

It is likewise possible to use a pretreated clay mineral. The pretreatment can be performed using an acid, in particular an inorganic acid, such as sulfuric acid, nitric acid or phosphoric acid, wherein sulfuric acid is particularly preferred.

The at least one second reactor has (as does also the first reactor) preferably a ratio of height:diameter (H:D) of 7:1, preferably 5.5:1.

More preferably, the oligomer melt introduced into the at least one second reactor has a temperature between 300° C. and 370° C., preferably 350° C. The oligomer melt is conducted from the bottom upward in the at least one second reactor gently in a temperature gradient having temperatures between 380° C. and 450° C., preferably 410° C. Correspondingly, the temperature in the reactor head is preferably in a range between 380° C. and 450° C., preferably 400° C. and 410° C.

It is preferred that the oligomers are cleaved into short-chain hydrocarbons having a molecular weight of <500 kg/mol in the at least one second reactor. In this case, the oligomers are cleaved into short-chain hydrocarbons that are in the gaseous state under the reaction conditions of the second reactor, preferably in the upper region of the at least one second reactor, i.e. in the reactor head of same. Typical short-chain hydrocarbons that are formed in the second reactor are C3→C22, preferably C3-C25 hydrocarbons, in particular unsaturated hydrocarbons that arise in various fractions as will later be explained in still more detail.

The oligomer melt entering into the at least one second reactor from the at least one first reactor can have a viscosity between 500 and 1500 mPas (350° C.), preferably between 500 and 1000 mPas (350° C.), particularly preferably between 600 and 800 mPas (350° C.), very particularly preferably between 650 and 700 mPas (350° C.).

The hydrocarbon fraction formed at the upper end of the at least one second reactor, that is to say in the reactor head of same, can have a viscosity between 50 and 300 mPas (410° C.), preferably between 100 and 250 mPas (410° C.), particularly preferably between 150 and 200 mPas (410° C.).

Owing to the decreasing viscosity of the oligomer mixture situated in the at least one second reactor—as already described for the first reactor—along the wall of the second reactor a lift is generated in the oligomer mixture and at the same time a downforce of the same in the reactor core (what is termed loop flow), wherein this effect is strengthened by an agitator. The agitator elements used in the at least one second reactor preferably correspond to the agitator elements for the at least one first reactor, just as the ratio of height to diameter.

The temperatures in the at least one first reactor and the at least one second reactor are more preferably adapted to the composition of the polymer starting mixture respectively used, wherein the temperature difference between the second reactor and the first reactor can be between 20 and 100° C., preferably between 30 and 70° C., particularly preferably between 40 and 60° C.

It is likewise possible and conceivable that not only are at least one first and at least one second reactor used, but also more than two, e.g. three or four, reactors arranged in parallel to one another are used.

In a further variant of the present method, short-chain gaseous hydrocarbons (e.g. C3 to >C22) that are formed in the reactor head of the at least one second reactor are preferably rapidly removed, via a pipe, preferably a heated pipe, to at least one precondenser, and the gaseous hydrocarbons that are cooled in the precondenser are introduced into the at least one main condenser for further cooling and condensation. The precondenser can be constructed in the form of a spiral tube heat exchanger.

In the at least one precondenser, the gaseous hydrocarbons are more preferably cooled to temperatures between 300 and 400° C., preferably 330 and 370° C., particularly preferably to 350° C., in order to suppress further unwanted secondary reactions, such as, for example, further degradation reactions. With the spontaneous cooling of the gaseous depolymerization products in the precondenser to 350° C., the depolymerization process is thereby ended and a significant shift of the product scale towards the liquid fraction is thereby prevented.

Owing to the cooling of the gaseous hydrocarbons in the precondenser, separation of paraffins (i.e. of predominantly higher saturated hydrocarbons having a chain length above C22) can occur, which are preferably removed in liquid or pasty form via a likewise heated pipe to at least one mixing vessel.

In the at least one mixing vessel (preferably designed as an agitator machine), the liquid paraffins separated off in the precondenser are more preferably blended or mixed with the reagent (here oligomer mixture) from the lower region of the at least one second reactor. The paraffins and oligomers are preferably mixed in the mixing vessel using a suitable agitator, such as, for example, a spiral agitator. In addition, the at least one clay mineral is introduced into the mixing vessel. The clay mineral, e.g. bentonite, is stirred in powder form into the mixture of paraffins, oligomers or microwaxes. As already described above, this pasty mixture of clay mineral, paraffins and oligomers is introduced via a heated pipe and a melt pump into the pipe between first and second reactor, using a Y-shaped special connecting piece.

The temperature of the mixture in the mixing vessel is preferably maintained at temperatures between 300° C. and 400° C., preferably 330° C. and 370° C., particularly preferably at 350° C.

However, it is also possible that the mixture of oligomers and paraffins (without clay mineral) which preferably has a temperature of 350° C., in addition is recirculated to the at least one second reactor using a melt pump into the reaction zone, i.e. preferably into the lower region/sump zone or else into the middle to upper region of the at least one second reactor, and again subjected to the cleaving process. The oligomer-paraffin mixture is preferably used as dispersant in the at least one second reactor.

In a variant of the following method, the gaseous hydrocarbons introduced into the main condenser from the at least one second reactor via a precondenser are condensed at temperatures between 15 and 30° C., preferably at 20° C., wherein virtually complete liquefaction of the gaseous hydrocarbons occurs. Non-condensable gases can either be combusted, e.g. by removal of the gases from the main condenser and introduction via a gas meter into a flare, or can be used for further energetic utilization for the system, or for other purposes, e.g. by means of a gas turbine.

The main condenser is preferably constructed as an inclined spiral tube heat exchanger. The inclination of 10-30°, preferably 20°, of the main condenser is selected for the optimum separation of the gaseous and liquid phases, and the draining thereof downwards. The temperatures in the head of the main condenser are preferably set at 20° C. to 25° C. Residual gases and volatile constituents of the depolymerization products of chain lengths C3 to C6 will thereby exit as gaseous constituents from the main condenser at the top. This off-gas is—as explained above—conducted via a heated pipe to the flare system and burnt there. The product drained off from the main condenser downwards into a product collection vessel is a synthetic product oil and consists of saturated and unsaturated hydrocarbons in a boiling range from 40° C. to 350° C., preferably 60 to 350° C.

Thus the product oil produced preferably comprises the hydrocarbon fractions of liquid gas (C3-C6), gasoline (C7-C10), kerosene (C11-C13), gas oil (C14-C19), heavy gas oil (C20-C22) and paraffins/microwaxes (>C22).

The quantitative proportion of the fractions differs depending on the waste polymer used and the thermolysis temperature employed in the at least one second reactor.

In general it may be stated that, at the lower thermolysis temperatures of, e.g. 385° C. or 400° C., the fraction of lower hydrocarbons (C3-C13) is greater than at higher temperatures, e.g. 415° C., at which the fraction of higher hydrocarbons (>C14) is, wherein the composition of the starting polymer blend has an effect on the quantitative fractions.

The present method therefore permits, by the choice of the thermolysis temperature in the second reactor, steering the product distribution towards a desired product group.

The condensate obtained from polypropylene (PP) preferably comprises oligomeric units of propene which are formed in the breakdown of the PP by cleavage of the C—C bonds. The PP condensate from the main condenser can typically comprise the following fractions:

liquid gas C3-C6, gasoline C7-C10, kerosene C11-C13, gas oil C14-C19, heavy gas oil C20-C22 and paraffins/microwaxes >C22. The products in this case extend over a wide chain length range of C3-C30. Thus, e.g. polypropylene (PP) is preferably cleaved as starting polymer into C3 monomers (C3), C3 dimers (C6), C3 trimers (C8-C10), C3 pentamers (C14-C16), C3 heptamers (C20-C22) and C3 nonamers (C26-C28). The main cleavage product is 2,4-dimethylhept-1-ene (C9).

As already mentioned, the quantitative composition of the product oil is determined by the starting polymers and also by the thermolysis temperatures in the second reactor.

Thus, a PP product oil obtained at a thermolysis temperature of 385° C. has, e.g. the following composition: approximately 8-12% by weight of paraffins/microwaxes >C22; approximately 8-12% by weight of heavy gas oil C20-C22; approximately 22-27% by weight of gas oil C14-C19; approximately 12-17% by weight of kerosene C11-C13; approximately 27-32% by weight of gasoline C7-C10 and approximately 8-12% by weight of liquid gas C3-C6.

A PP product oil obtained at a thermolysis temperature of 400° C. has, e.g. the following composition: approximately 22-27% by weight of paraffins/microwaxes >C22; approximately 8-12% by weight of heavy gas oil C20-C22; approximately 18-22% by weight of gas oil C14-C19; approximately 12-17% by weight of kerosene C11-C13; approximately 22-27% by weight of gasoline C7-C10 and approximately 3-7% by weight of liquid gas C3-C6.

A PP product oil obtained at a thermolysis temperature of 415° C. has, e.g. the following composition: approximately 28-32% by weight of paraffins/microwaxes >C22; approximately 8-12% by weight of heavy gas oil C20-C22; approximately 22-27% by weight of gas oil C14-C19; approximately 8-12% by weight of kerosene C11-C13; approximately 18-22% by weight of gasoline C7-C10 and less than approximately 5% by weight of liquid gas C3-C6.

A condensate obtained from polyethylene (PE) preferably comprises hydrocarbons in a chain length range of C3-C30. The PE condensate typically comprises n-alkanes and n-alkenes (olefins) in a ratio of 50:50. Thus, the hydrocarbons are always present in parallel in the saturated and unsaturated form such as, e.g. C10: n-undecene and undec-1-ene.

A PE product oil obtained at a thermolysis temperature of 400° C. has, e.g. the following composition: traces of paraffins/microwaxes >C22; traces of heavy gas oil C20-C22; approximately 28-32% by weight of gas oil C14-C19; approximately 18-22% by weight of kerosene C11-C13; approximately 42-47% by weight of gasoline C7-C10 and approximately 5-10% by weight of liquid gas C3-C6.

A PE product oil obtained at a thermolysis temperature of 410° C. has, e.g. the following composition: traces of paraffins/microwaxes >C22; less than 5% by weight of heavy gas oil C20-C22; approximately 42-47% by weight of gas oil C14-C19; approximately 12-17% by weight of kerosene C11-C13; approximately 28-32% by weight of gasoline C7-C10 and approximately 5-10% by weight of liquid gas C3-C6.

A PE product oil obtained at a thermolysis temperature of 415° C. has, e.g. the following composition: traces of paraffins/microwaxes >C22; less than 5% by weight of heavy gas oil C20-C22; approximately 42-47% by weight of gas oil C14-C19; approximately 12-17% by weight of kerosene C11-C13; approximately 28-32% by weight of gasoline C7-C10 and approximately 5-10% by weight of liquid gas C3-C6.

A PE product oil obtained at a thermolysis temperature of 420° C. has, e.g. the following composition: approximately 3-7% by weight of paraffins/microwaxes >C22; approximately 8-12% by weight of heavy gas oil C20-C22; approximately 42-47% by weight of gas oil C14-C19; approximately 12-17% by weight of kerosene C11-C13; approximately 22-27% by weight of gasoline C7-C10 and approximately 5-10% by weight of liquid gas C3-C6.

In a further preferred embodiment, the condensate or product oil leaving the main condenser is fed to a distillation for separation of the condensate into fractions having different boiling points. In this case, the main condenser is dispensed with and is replaced by a distillation column (fractional distillation). Here, the fractions "heating oil" and gasoline are separated. Fractional columns are familiar technologies and are widely used. The dimensioning of the fractional columns is preferably adapted to the boiling ranges of the individual fractions, wherein column height, volume, plate count and/or head condenser of the column are variable.

The condensate or product oil leaving the main condenser can be collected in a collection vessel and then preferably be fed to a distillation or rectification which effects a separation of the product oil into a gasoline-like fraction and a heating oil-like fraction.

Correspondingly, a system for carrying out the described method comprises
- at least one extruder for melting the synthetic polymers,
- at least one melt filter that is for purifying the polymer melt and is arranged downstream of the extruder,
- at least one first reactor for breaking down the polymers into oligomers that is arranged downstream of the melt filter,
- at least one second reactor arranged downstream of the at least one first reactor for breaking down the oligomers formed in the at least one first reactor into gaseous hydrocarbons,
- at least one precondenser arranged downstream of the at least one second reactor for precooling the short-chain gaseous hydrocarbons leaving the second reactor, and
- at least one main condenser arranged downstream of the at least one precondenser for condensation of the gaseous hydrocarbons that are precooled in the at least one precondenser.

The reaction conditions described for the present method and the designs of the individual parts and/or components of the following system associated therewith are correspondingly applicable, in such a manner that reference is made thereto to a repetition hereinafter.

In a variant of the following system, at least one first reactor and the at least one second reactor used each have at least two controllable heating zones, preferably at least three to five controllable heating zones. The heating zones are adjusted by heaters arranged in the wall of the reactors. In each heating zone, temperature sensors are provided which transmit the respective current temperatures in the corresponding heating zone to the plant controller. The number of heating zones can be set as desired in terms of temperature and is in particular dependent on the composition of the polymer melt that is to be broken down. Also, the number of heating zones in the at least one first reactor can be identical or different to the number of heating zones in the at least one second reactor. It is possible to set a temperature gradient in the reactors via the heating zones, where the temperature within the reactors increases from bottom to top.

Furthermore, the at least one first reactor and the at least one second reactor each have an agitator element in the form of a spiral agitator, an anchor agitator, a screw, or a combination thereof, wherein both reactors preferably have an agitator element in the form of a combination of spiral agitator and screw.

In a preferred embodiment, the inner walls and internals of the at least one first reactor and/or of the at least one second reactor have at least one ceramic coating. Such a ceramic coating has proved to be advantageous, since the process of coking can be greatly reduced thereby. Reactors made of stainless steel, under the same process conditions exhibit a carbon formation on the inner walls of the reactors, even though this is decreased by the use of the special agitator elements. It has additionally been found that steel alloys promote an unwanted catalytic decomposition process on the short-chain hydrocarbon molecules, C3-C22 hydrocarbons, to form carbon and hydrogen. To avoid this effect, a complete inertization by means of a ceramic inner coating of the affected system components can be provided. The components to be coated, in addition to the inner walls of the first and/or second reactor, are the surfaces of the agitator elements respectively used in the reactors, the pipe between first and second reactor, the pipe between second reactor and precondenser, the inner walls of the precondenser and the cooling elements in the precondenser. The ceramic coating preferably has a thickness between 1 and 5 mm, preferably 1 and 2 mm thickness. The ceramic coating is chemically inert, temperature-stable up to 550° C. and heat-permeable. Contacts in the critical temperature ranges between the polymer melt and the cracking gases with the stainless steel surface are thereby excluded. The ceramic coating in addition is distinguished by a long service life, withstands mechanical stresses (scratch- and impact-resistant) and counteracts soil deposits. This additionally effects a prolongation of the periods between maintenance intervals and a simplification of the cleaning of the coated components in the context of maintenance. Preferred ceramic coatings are based on silicon carbides. Thus, e.g. Si-doped silicon carbide is characterized by a high hardness, heat conductivity, chemical resistance and corrosion resistance.

The reactor heads of the first and/or second reactor preferably have the shape of a "bubble" expanded in diameter, in order to permit the depolymerization products to flow off better from the melt and collection and flow-calming of the gaseous depolymerization products before they are passed on to the precondenser. In addition, the possibility is to be provided that any melt particles entrained during the off-gassing of the depolymerization products can pass back into the melt.

In addition, it is preferred when the at least one first reactor and the at least one second reactor are blanketed by at least one protective gas, in particular nitrogen, in such a manner that the process of polymer breakdown can take place under a protective gas atmosphere.

The present system and therefore also the present method can be operated at a pressure between 0.4 and 5 bar, preferably between 1 and 4 bar. Particular preference is given to operation of the system under a standard pressure at 1 bar, in such a manner that pressurization and the apparatus costs associated therewith can be avoided.

In addition, the present system including the piping, is preferably temperature-controlled and heat-insulated.

In a variant of the present system, between the at least one second reactor and the at least one main condenser, at least one precondenser is arranged, e.g. in the form of a spiral tube heat exchanger for precooling the gaseous hydrocarbons leaving the at least one second reactor.

It is also preferred that the at least one precondenser is connected to at least one mixing vessel for receiving the paraffins formed in the at least one precondenser during the precooling of the gaseous hydrocarbons leaving the at least one second reactor.

Also, the present system preferably has at least one control unit for controlling the feed rate of the polymers to the at least one extruder. This at least one control unit preferably comprises in each case a weighing appliance for monitoring the fill level of the at least one first reactor and of the at least one second reactor. The metering of the feed rate of the synthetic polymers that are to be broken down to the extruder preferably proceeds via the breakdown rate measured in the at least one first reactor and in the at least one second reactor.

The control unit also permits the controlling of the temperature of the system. In this case, the pressure upstream of the melt filter, the temperatures along the hot sections, i.e. along the heated tubes between the individual reactors, the individual temperature zones in the at least one first reactor and in the at least one second reactor and also in the mixing vessel are measured and monitored. From the measured values, the open-loop and closed-loop control of all heating systems is defined. The control unit therefore permits running or operation of the system with freely selectable temperature profiles, which are adjustable in dependence on the polymer blend used.

It is likewise possible that, between the at least one first reactor and the at least one second reactor, at least one buffer vessel is arranged which acts as safety vessel. The at least one buffer vessel is more preferably cooled, in order in an emergency to guarantee rapid cooling down of the polymer melt situated in the at least one first reactor and in the at least one second reactor when removing same to the buffer vessel. For this purpose, between the system and the buffer vessel, at least one pressure valve is installed which opens in the event of flash fires and releases the way for gases or also possibly polymer melt etc. in the vessel.

In a further preferred embodiment of the present system and of the present method, compensators are used, e.g. in the form of flexible components, e.g. made of stainless steel. The compensators can be heatable. Thus, the compensators can have, e.g. heating mantles in the form of removable sleeves and also additional seals in the form of removable protective mantles.

As already described above, the present method, in particular when a fractional distillation is carried out, permits the production of a heating oil fraction and a gasoline fraction.

The heating oil produced is characterized by a particularly low sulfur fraction and a flashpoint elevated in comparison with standard heating oil. Thus, the flashpoint of a heating oil obtained from a PE/PP mixture (50:50) (as specified in EN ISO 2719) is between 70° C. and 90° C., preferably between 75° C. and 90° C., and the sulfur fraction (as specified in EN ISO 20846, EN ISO 20884) is between 1 and 20 mg per kilogram, preferably between 1 and 15 mg/kg.

In comparison with that of the heating oil produced by means of the method, a standard heating oil obtained from petroleum has a flashpoint of 55 to 60° C.

The heating oil fraction obtained by the present method has a high fraction of C13-C18, in particular unsaturated, hydrocarbons, whereas standard heating oil obtained from petroleum has an elevated fraction of C11-C13 hydrocarbons.

Thus the fraction of C13-C18 hydrocarbons in the heating oil fraction obtained by the present method can be between 5 and 20 parts/% by weight, preferably 8 and 18 parts/% by weight. The fraction of C13-C16 hydrocarbons can even be between 10 and 20 parts/% by weight, preferably between 11 and 18 parts/% by weight.

The heating oil fraction obtained can be used, in particular, for stationary internal combustion engines or in power plants.

The gasoline fraction produced by means of the present method has a high fraction of lower, predominantly unsaturated, C6-C12 hydrocarbons and only small amounts of higher hydrocarbons are present. The fraction of C9 hydrocarbons in the gasoline fraction can be, e.g. 30-40, preferably 34-38, parts/% by weight. The olefinic content is preferably at values greater than 90%.

The preferred field of use of the gasoline fraction obtained by the present method is in the sector of bulk chemicals. For instance, the gasoline fraction, owing to the high fraction of unsaturated lower hydrocarbons, can be used in polymer chemistry.

BRIEF DESCRIPTION OF THE DRAWINGS

The invention is described hereinafter in more detail with reference to an exemplary embodiment, using the drawings of the figures. In the drawings:

FIG. 7a shows an embodiment of a tube having a connecting piece S for feeding in a mixture containing a clay mineral into the melt in the pipe between first and second reactor, and FIG. 7b shows a plane view onto the viewing plane A-A of connecting piece S.

DETAILED DESCRIPTION OF THE INVENTION

First Exemplary Embodiment

Figure 1:
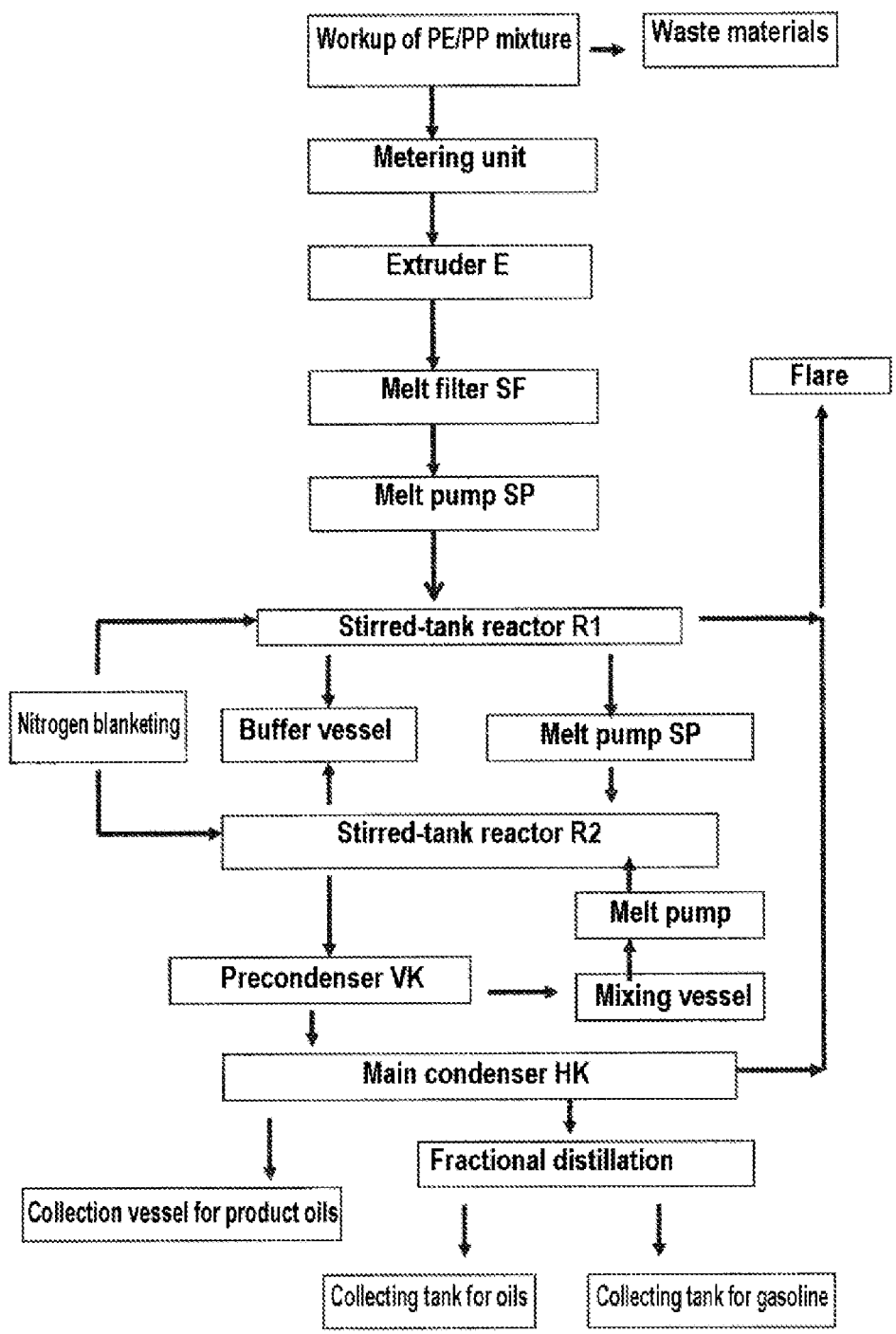
FIG. 1 shows a process flowchart of at least one embodiment of the present method.

FIG. 1 shows a process flowchart of a first embodiment of the present method. The basis of the method is a polyolefin mixture having a fraction of >95% of polyethylene and polypropylene, which polyolefin mixture is comminuted and purified by removal of waste material such as minerals, metals, fibers, papers and plastics. The methods known therefor are known to those skilled in the art. The waste materials are either fed to the wash water, in the event that they are biogenic waste materials, or are subjected to other disposal measures.

The PE/PP mixture that is worked up is fed continuously to an extruder E via a metering unit as feed appliance Z. In the extruder E, the PE/PP mixture is melted by heating to 300° C., wherein, at the same time, residual moisture is removed from the polymer blend and a degassing follows.

The molten PE/PP mixture in the extruder E is transported via a heated pipe into or through the melt filter SF, in which the PE/PP melt is freed from residual traces of minerals, metals and fibers.

The highly pure PE/PP melt exiting from the melt filter SF is then introduced by means of a melt pump, which, as with all of the melt pumps used in the method, also acts as a return barrier, in the lower region (sump region) of the first stirred-tank reactor R1 at a temperature of 300° C. The first stirred-tank reactor R1 has a maximum capacity of 120 l and a ratio of height to diameter of 5.5:1. The stirred-tank reactor R1 is equipped with five separately controllable heating zones HZ1-HZ5 and comprises an agitator element which is a combination of spiral agitator and screw. The agitator is fitted with a (plurality of) temperature measuring sensor(s) in the agitating shaft. The sump outlet of the first reactor R1 is heated and the fill level of the first reactor R1 is measured by a weighing appliance.

In the first stirred-tank reactor R1, the PE/PP polymer blend is gently and evenly conducted from the lower (sump region) to the upper (head region) region of the reactor and in the course of this heated stepwise to 350° C. The initial viscosity of the PE/PP polymer blend in the lower region (sump region) of the reactor R1 is $1.5 \cdot 10^6$ MPas (300° C.). Owing to the stepwise heating of the polymer blend in the reactor R1 during the lift along the wall of the reactor, the polymer blend is broken down to oligomers under mild conditions.

The oligomer blend arriving at the reactor head of the stirred-tank reactor R1 has a temperature of 350° C. and an initial viscosity of 671 MPas (350° C.). In addition to the breakdown of the PE/PP polymers to the corresponding oligomers, in the stirred-tank reactor R1, likewise the formation of small amounts of gaseous hydrocarbons can occur, which are in the present case removed to the flare.

From the stirred-tank reactor R1, the reagent (oligomer mixture) is transported via a heated pipe using a melt pump at 350° C. to the lower region (sump region) of the stirred-tank reactor R2.

In the stirred-tank reactor R2, the reagent, under mild conditions and uniformly, is conducted from the lower region (sump region) of the reactor R2 to the upper region (head region) of the reactor R2 and heated to a maximum of 410° C. The viscosity that decreases in the course of this generates a lift of the oligomer mixture at the wall and a simultaneous downforce in the core.

The oligomer mixture of PE and PP is further cleaved to form short-chain hydrocarbons in an accurately targeted manner in the upper region (head region) of the reactor R2, i.e. the reactor head. The PE/PP oligomer mixture which is introduced into the stirred-tank reactor R2 from the stirred-tank reactor R1 has an initial viscosity of 671 MPas (350° C.). On account of the further breakdown and/or further polymer degradation, the viscosity decreases within the stirred-tank reactor R2 to a viscosity at the reactor head of 200 MPas (410° C.). The conversion rate of the oligomer mixture to gaseous hydrocarbons in the second stirred-tank reactor R2 is approximately 50 l/h.

The gaseous hydrocarbons that are formed in the upper region of the stirred-tank reactor R2 are introduced directly into the precondenser VK or preseparator and there cooled to 350° C. The rapid decrease in temperature of the gaseous hydrocarbons from 410° C. to 350° C. suppresses further unwanted secondary reactions, in particular degradation reactions, by termination of the thermal free radical formation.

The paraffins subsequently separated off in the precondenser VK, i.e. predominantly alkanes having the general empirical formula $C_nH_{2n+2}$, wherein n is between 18 and 32, preferably >22, are removed from the precondenser VK to the mixing vessel M, in which the paraffins are admixed with reagent (oligomer mixture) from the lower region (sump region) of the stirred-tank reactor R2. The temperature of the mixing vessel M is held at 350° C. by means of heating. The mixture of oligomer reagent and paraffins is metered using a melt pump via a heated pipe directly into the reaction zone (reactor head) of the stirred-tank reactor R2. This process step prevents further breakdown of the olefin molecules, the occurrence of paraffins in the product oil, and in particular the return of degradable oligomers/paraffins to the breakdown process, and increases the yield of product oil.

The gaseous hydrocarbons pass from the precondenser VK to the main condenser HK and condense there to form a product oil having an exit temperature of approximately 20° C. Non-condensable gases are passed through a gas meter for measuring the volumetric flow rates into the flare. It is likewise possible not to burn these gases, but to use them for the system by means of a gas turbine for energetic utilization.

The stirred-tank reactor R1 and the stirred-tank reactor R2 are each blanketed with nitrogen, in such a manner that the depolymerization of the PE/PP starting mixture takes place wholly in a nitrogen atmosphere and unwanted oxidations do not occur.

Between the stirred-tank reactor R1 and the stirred-tank reactor R2, in addition, a buffer vessel is arranged which serves as cooled safety container. A pressure valve installed between the system and the container opens in the event of flash fires and opens the path for gases etc. into the buffer container.

The synthetic product oil obtained from the main condenser is separated in a subsequent fractional distillation into a gasoline fraction and a heating oil fraction.

Figure 2A:
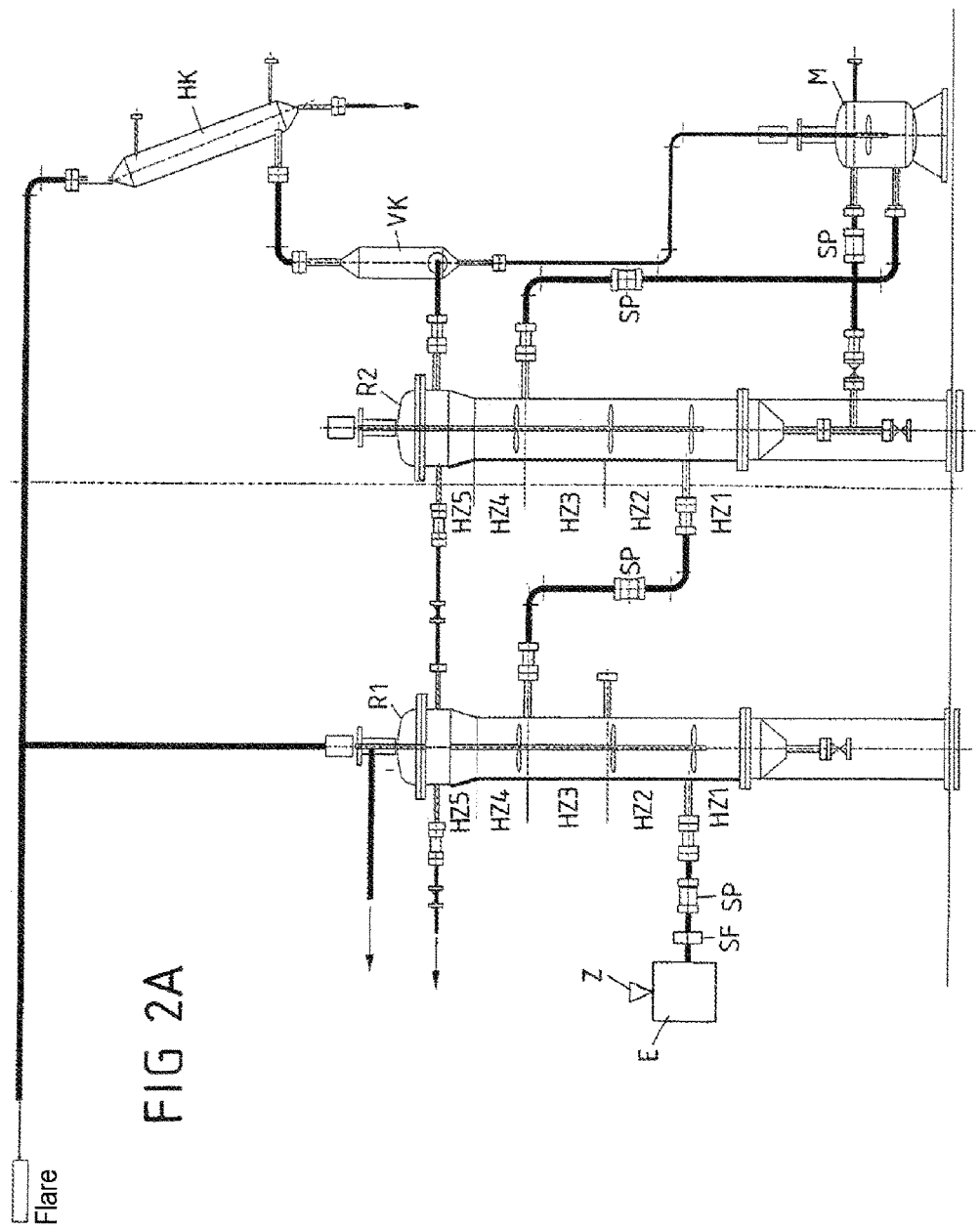
FIG. 2a shows a schematic drawing of the structure of a first embodiment of the present system.

In FIG. 2a, a schematic drawing of the structure of a system as per the first embodiment is shown. On the functioning of the system reference is substantially made to the description cited above for the process diagram of FIG. 1.

In the first embodiment, not only the first stirred-tank reactor R1, but also the second stirred-tank reactor R2 have five heating zones, wherein this number can also vary.

Second Exemplary Embodiment

Figure 2B:
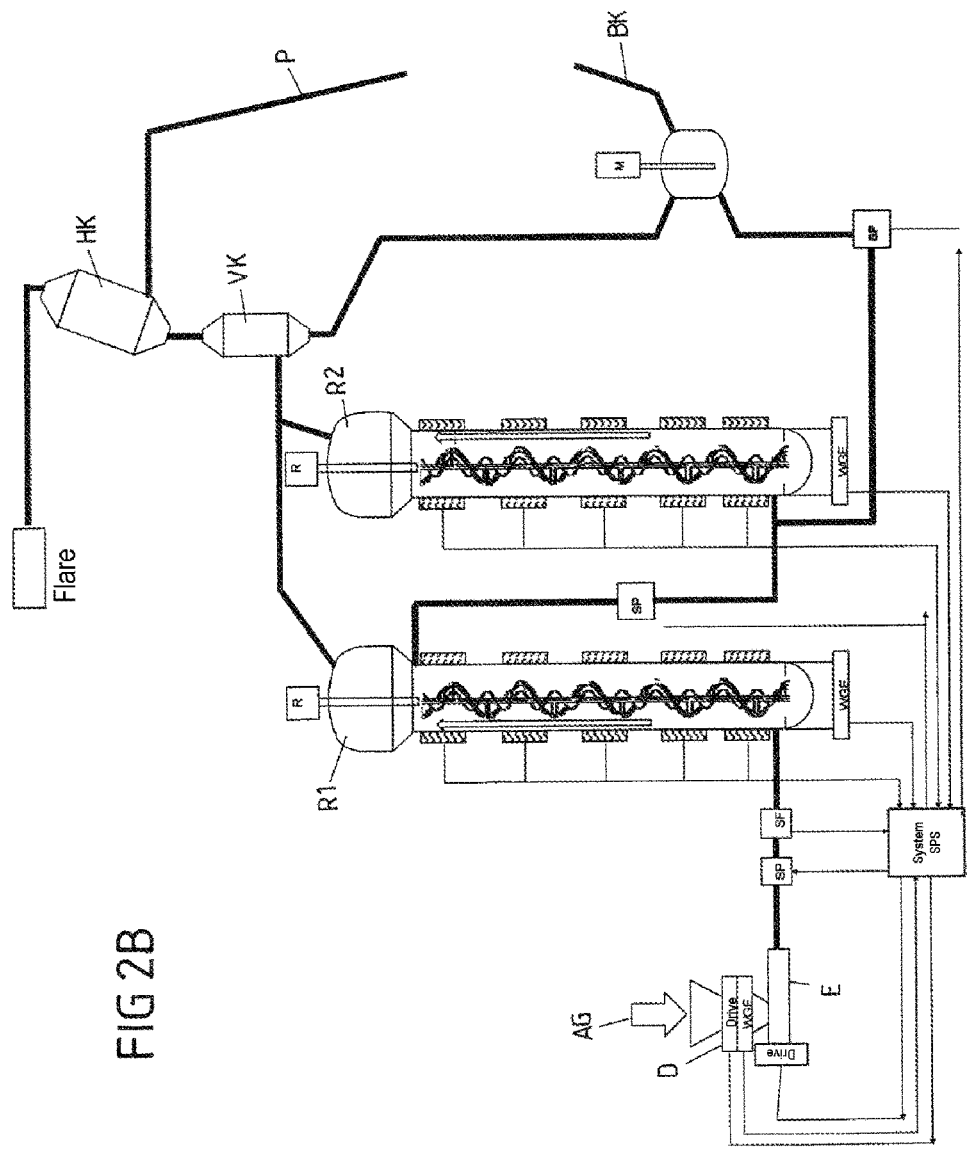
FIG. 2b shows a schematic drawing of the structure of a second embodiment of the present system.

FIG. 2b shows a schematic drawing of a second embodiment of the system according to the invention.

As described above, the prepared scrap plastic shreds are subjected to a preagglomeration and thereby achieve a consistency which permits introduction into the system. This preagglomerated waste plastic AG is placed into a metering apparatus D having a screw drive and weighing appliance WGE. The screw drive and the weighing appliance WGE are connected to the central system SPS not only as signal transmitters but also as signal receivers. In this metering appliance, at the same time, further drying and preheating take place. Beneath the metering appliance, a heated twin-screw extruder E is arranged, which warms, compacts and melts the raw material from 20° C. to >200° C. Via a heated pipe, the pasty raw material is further heated and transported to a melt pump SP. This melt pump SP forces the raw material into the system and at the same time prevents backflow of the melt to the extruder E. Immediately downstream of the melt pump SP, the melt filter SF with a fine-mesh exchangeable fabric filter is arranged. The functionality of the melt filter is monitored by an upstream pressure sensor which in turn is connected to the system SPS.

The plastics melt thus purified is introduced into the first reactor R1 in the sump region. The plastics melt, at the entry into the reactor R1 has a temperature of 300° C. and a viscosity of 150 Pas. The reactor R1 stands on a weighing appliance WGE, which at all times reports the current filling level of the reactor R1 to the system SPS. The reactor R1 is lined with a ceramic layer in order to prevent direct contact between the melt and the metallic reactor wall. The reactor R1 is constructed as a slim reactor having a diameter/length ratio of 1:5.5 to 1:7.

On the cylindrical wall of the reactor R1, 3 to 5 independently acting heaters are mounted. In each associated heating zone, temperature sensors are arranged which report the respective currently effective temperature on the wall of the reactor R1 in this heating zone to the system SPS. The system SPS controls the heaters in such a manner that, in the cylindrical part of the reactor R1, from the sump to the head, a continuously increasing temperature gradient is formed. This continuously rising temperature in the reactor R1 forces a laminar melt flow continuously flowing upwards.

The upwardly directed laminar melt flow is supported by an agitator, the flights of which are designed in such a manner that the upward flow is supported. This flow design displaces a possible depolymerization to the head region of the reactor R1. Any gaseous depolymerization products already formed are immediately transported by the laminar flow to the head region and thus a foaming of the melt is prevented.

At the head of the reactor R1, the melt reaches a temperature of 340° C. to 360° C. and a viscosity of 1.5 Pas. By this temperature regime and by feeding in a bentonite catalyst, first into the reactor R2, in the reactor R1 only a small part of the melt is converted to gaseous depolymerization products. The remaining melt undergoes a precracking. The gaseous depolymerization products formed in the reactor R1 are passed via a heated pipe to the precondenser.

From the head region of the reactor R1, the melt is passed to the reactor R2 via a heated pipe and a melt pump SP. The melt enters into the sump zone of the reactor R2 at a temperature of 350° C. and a viscosity of 1.5 Pas.

On entry of the melt into the reactor R2, said melt is mixed by a specially designed connecting piece with the mixture of bentonite catalyst, paraffins and microwaxes coming from the mixing vessel M. This specially designed connecting piece is constructed as a "Y-shaped tube", wherein the feed of the mixture which comes from the mixing vessel M is conducted into the core zone of the tube in which the melt is fed from the reactor R1 (see in this context also FIG. 7a, b).

The reactor R2 stands on a weighing appliance WGE which at all times reports the current filling level of the reactor 2 to the system SPS. The reactor R2 is likewise lined with a ceramic layer in order to prevent direct contact between the melt and the metallic reactor wall. The reactor 2 is constructed as a slim reactor having a diameter/length ratio of 1:5.5 to 1:7.

On the cylindrical wall of the reactor 2, three to five heaters independently acting are mounted. In each heating zone, temperature sensors are arranged which report the respective currently effective temperature on the wall of the reactor 2 in this heating zone to the system SPS. The system SPS controls the heaters in such a manner that, in the cylindrical part of the reactor R2, from the sump to the head a continuously rising temperature gradient is formed. This continuously rising temperature in the outer region of the reactor R2 forces a laminar melt flow continuously flowing upwards. The upwardly directed laminar melt flow is supported by an agitator, the flights of which are designed in such a manner that the flow in the outer region of the reactor R2 is supported upwards and in the inner region of the reactor R2 a downwards-directed flow is supported. With this flow configuration, the depolymerization is displaced to the head region of the reactor R2. Gaseous depolymerization products formed are immediately transported by the laminar flow to the head region and thus foaming of the melt is prevented.

At the head of the reactor R2, the melt reaches a temperature of 400° C. to 410° C. and a viscosity of 0.1 Pas. Any melt fractions that are still not depolymerized are transported by the action of the specially designed agitator in the center of the reactor 2 downwards to the sump region of the reactor 2 and then participate again in the depolymerization in the outer laminar upwards flow.

The information from the weighing appliances WGE of the reactors R1, R2 are converted in the system SPS into orders to the drives of the metering appliance D, of the twin-screw extruder E and of the melt pumps SP in such a manner that the present system can operate continuously.

The head zones of the reactors R1, R2 are constructed as a "bubble" of extended diameter, in order to permit better flow of the depolymerization products off from the melt and collection and flow-calming of the gaseous depolymerization products before they are passed on to the precondenser. In addition, there is to be the possibility that any melt particles entrained during the off-gassing of the depolymerization products can pass back into the melt.

The gaseous depolymerization products of chain length C3 to >C22 that are being formed in the reactor R2 are passed via a heated pipe to the precondenser VK. The precondenser VK is constructed as a spiral tube heat exchanger. In this precondenser VK, the volatile depolymerization products of chain lengths greater than C22 are condensed out. These paraffins, microwaxes and hydrocarbon chains above C22 are passed downwards as a pasty or liquid phase, as system-relevant intermediates, via a heated pipe, to a mixing vessel M.

The still-volatile depolymerization constituents of chain lengths C3 to C22 at the head of the precondenser VK are conducted into the main condenser HK lying thereabove. This main condenser HK is constructed as an inclined spiral tube heat exchanger. The inclination of 20° C. of the main condenser is selected for the optimum separation of the gaseous and liquid phases and the draining downwards thereof. The temperatures in the head of the main condenser HK are set at 20° C. to 25° C. Therefore, residual gases and volatile constituents of the depolymerization products of chain lengths C3 to C6 will exit from the main condenser at the top as gaseous constituents. This off-gas is conducted via a heated pipe to the flare system and burnt there. The product that flows off from the main condenser HK downwards into a product collection vessel P is a synthetic product oil and consists of saturated and unsaturated hydrocarbons in a boiling range from 40° C. to 350° C. and comprises the hydrocarbon fractions from C7 to C22.

The mixing vessel M is constructed as an agitator machine, which operates at a constant temperature of 340° C. to 350° C. by heating/cooling, at which the condensate from the precondenser VK is kept in a pasty state. The pulverulent bentonite catalyst BK is mixed into this pasty condensate with constant stirring. This pasty mixture of condensate and bentonite condenser is introduced into the reactor 2 via a heated pipe and a melt pump SP. This introduction proceeds via the already abovedescribed Y-shaped special connecting piece (see also FIGS. 7a, b).

FIGS. 7a, b show the detailed structure of the Y-shaped special connecting piece S and the arrangement thereof in the pipe between first reactor R1 and second reactor R2. The special connecting piece S is constructed in a fan shape. This specific fan-shaped construction of the connecting piece S permits an optimum mixing of the oligomer mixture with the mixture from the mixing vessel M containing the clay mineral.

Figure 3:
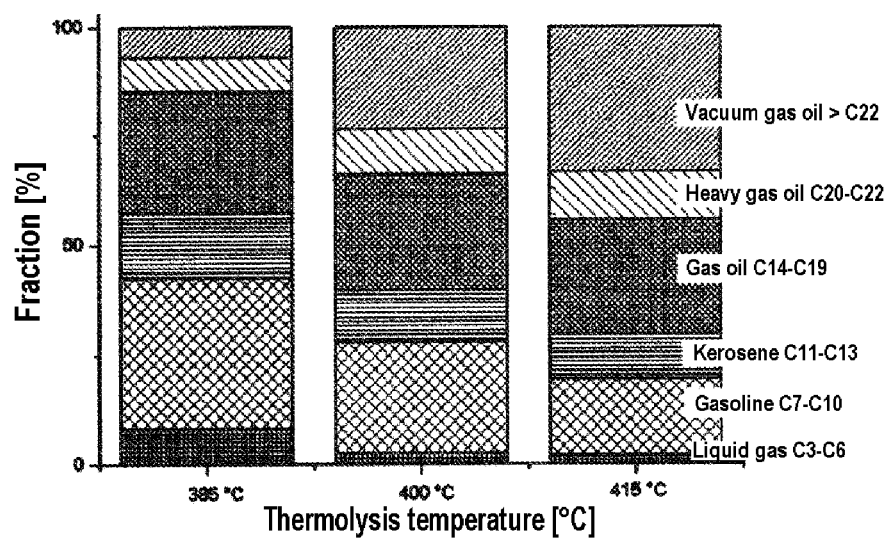
FIG. 3 shows a composition of a product oil obtained from polypropylene (PP) at various thermolysis temperatures.

FIG. 3 is a diagram from which the composition of condensates or product oils obtained from PP is shown in dependence on the thermolysis temperature employed in the second reactor R2.

The components obtained in the breakdown of PP are virtually exclusively oligomeric units of propene and form in the breakdown of polypropylene by cleavage of C—C bonds. The products extend over a wide chain length range of C3-C30. As main cleavage product, in all experiments, independently of the thermolysis temperature, 2,4-dimethylhept-1-ene was found.

In total, the components can be subdivided into 6 fractions: liquid gas (C3-C6), gasoline (C7-C10), kerosene (C11-C13), gas oil (C14-C19), heavy gas oil (C20-C22) and paraffins/microwaxes (>C22).

As can be seen from the diagram of FIG. 3, at relatively high thermolysis temperatures, more high boilers (higher hydrocarbons) occur in the condensate. At the same time, the fraction of low boilers (lower hydrocarbons) falls. This is particularly marked for the gasoline and vacuum gas oil (paraffins/microwaxes) fractions.

Whereas at 385° C., the gasoline fraction dominates at approximately 30%, and the fraction of vacuum gas oil is vanishingly small, at 410° C., the paraffins/microwaxes fraction dominates at a similar fraction and the gasoline fraction is only half as great. The middle fractions of kerosene, gas oil and heavy gas oil remain approximately constant. By varying the thermolysis temperature, therefore, it is possible to a certain extent to steer the product distribution towards a desired product group.

Thus, a PP product oil obtained at a thermolysis temperature of 385° C. has, e.g., the following composition: approximately 10% by weight of paraffins/microwaxes >C22; approximately 10% by weight of heavy gas oil C20-C22; approximately 25% by weight of gas oil C14-C19; approximately 15% by weight of kerosene C11-C13; approximately 30% by weight of gasoline C7-C10 and approximately 10% by weight of liquid gas C3-C6.

A PP product oil obtained at a thermolysis temperature of 400° C. has, e.g., the following composition: approximately 25% by weight of paraffin/microwaxes >C22; approximately 10% by weight of heavy gas oil C20-C22; approximately 20% by weight of gas oil C14-C19; approximately 15% by weight of kerosene C11-C13; approximately 25% by weight of gasoline C7-C10 and approximately 5% by weight of liquid gas C3-C6.

A PP product oil obtained at a thermolysis temperature of 415° C. has, e.g., the following composition: approximately 30% by weight of paraffins/microwaxes >C22; approximately 10% by weight of heavy gas oil C20-C22; approximately 25% by weight of gas oil C14-C19; approximately 10% by weight of kerosene C11-C13; approximately 20% by weight of gasoline C7-C10 and less than approximately 5% by weight of liquid gas C3-C6.

Figure 4:
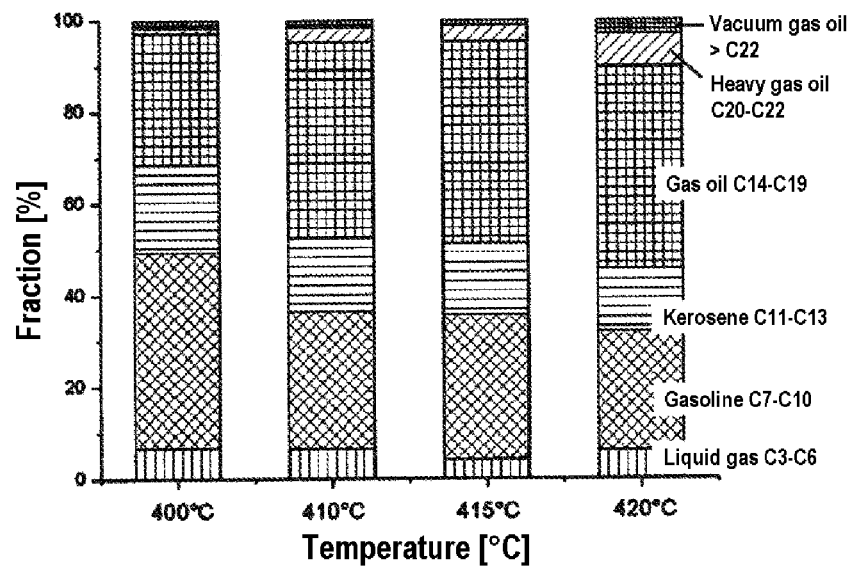
FIG. 4 shows a composition of a product oil obtained from polyethylene (PE) at various thermolysis temperatures.

The diagram shown in FIG. 4 relates to the composition of condensates and product oils obtained from PE. The products obtained from PE extend over about a chain length range of C3-C30. The quantitative analysis of the condensates obtained shows that the distribution of the individual heating value fractions with the use of PE varies in dependence on the thermolysis temperature at which the condensates were obtained. As can be seen from FIG. 4, the fraction of gas oil (C14-C19) increases with increasing temperature, whereas the fraction of the lower hydrocarbon fractions such as kerosene (C11-C13) and gasoline (C7-C10) decreases.

A condensate obtained from polyethylene (PE) preferably comprises hydrocarbons in a chain length range of C3-C30. The PE condensate typically comprises n-alkanes and n-alkenes (olefins) in a ratio of 50:50. Thus, the hydrocarbons are always present in parallel in the saturated and unsaturated form such as, e.g., C10:n-undecene and undec-1-ene.

A PE product oil obtained at a thermolysis temperature of 400° C. has, e.g., the following composition: traces of paraffins/microwaxes >C22; traces of heavy gas oil C20-C22; approximately 30% by weight of gas oil C14-C19; approximately 20% by weight of kerosene C11-C13; approximately 45% by weight of gasoline C7-C10 and approximately 5-10% by weight of liquid gas C3-C6.

A PE product oil obtained at a thermolysis temperature of 410° C. has, e.g., the following composition: traces of paraffins/microwaxes >C22; less than 5% by weight of heavy gas oil C20-C22; approximately 45% by weight of gas oil C14-C19; approximately 15% by weight of kerosene C11-C13; approximately 30% by weight of gasoline C7-C10 and approximately 5-10% by weight of liquid gas C3-C6.

A PE product obtained at a thermolysis temperature of 415° C. has, e.g., the following composition: traces of paraffins/microwaxes >C22; less than 5% by weight of heavy gas oil C20-C22; approximately 45% by weight of gas oil C14-C19; approximately 15% by weight of kerosene C11-C13; approximately 30% by weight of gasoline C7-C10 and approximately 5-10% by weight of liquid gas C3-C6.

A PE product oil obtained at a thermolysis temperature of 420° C. has, e.g., the following composition: approximately 5% by weight paraffins/microwaxes >C22; approximately 10% by weight of heavy gas oil C20-C22; approximately 45% by weight of gas oil C14-C19; approximately 15% by weight of kerosene C11-C13; approximately 25% by weight of gasoline C7-C10 and approximately 5-10% by weight of liquid gas C3-C6.

Figure 5:
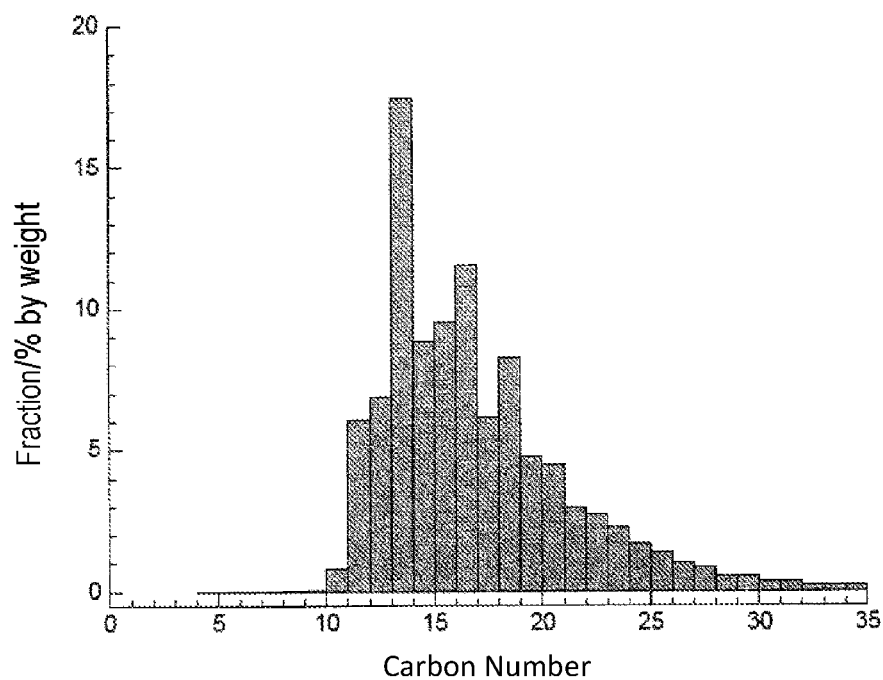
FIG. 5 shows a graph of the quantitative composition of the heating oil fraction produced by the present method.
Figure 6:
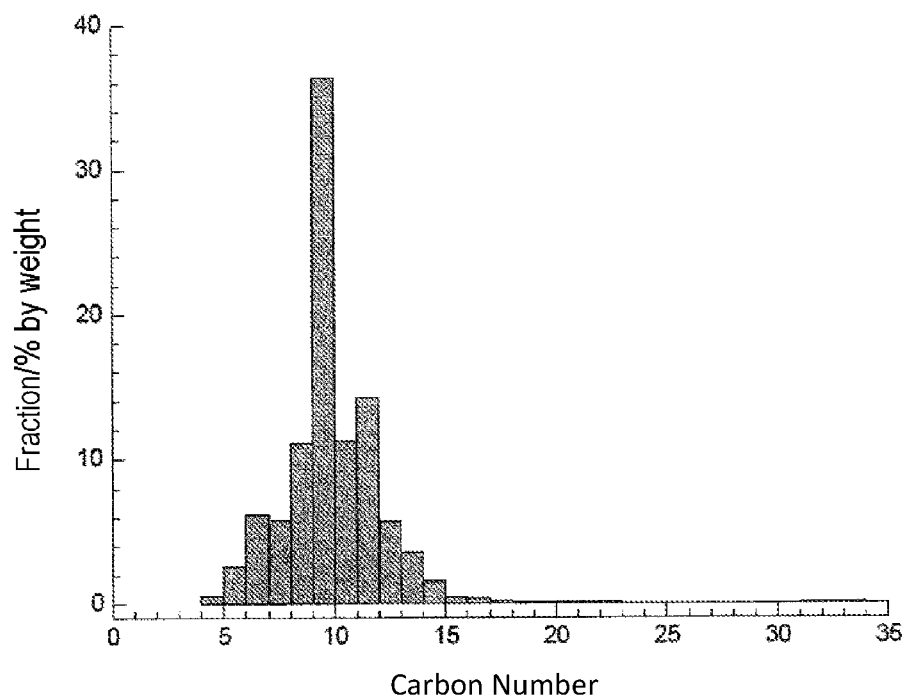
FIG. 6 shows a graph of the quantitative composition of the gasoline fraction produced by the present method.

FIGS. 5 and 6 each contain the quantitative compositions of the heating oil fraction and gasoline fraction obtained after fractional distillation.

Thus, the heating oil fraction obtained by the present method has a high fraction of C13-C18, in particular unsaturated, hydrocarbons (FIG. 5). In the present example, the fraction of C13 hydrocarbons is particularly high at approximately 18% by weight. Also C14-C18 hydrocarbons are represented with fractions between 8 and 12% by weight, whereas the hydrocarbons of C<11 are only detectable in very low amounts, or are not detectable at all.

FIG. 6 shows the quantitative composition of an exemplary gasoline fraction. Thus, the gasoline fraction comprises, in significant amounts, C6-C12 hydrocarbons, wherein the fraction of C8-C11 hydrocarbons is increased. Thus, the fraction of C9 hydrocarbons is, e.g., approximately 36% by weight.

The invention claimed is:

1. A method for breaking down polyolefins, comprising the steps of:
   a) producing a polymer melt of polyolefins;
   b) purifying the polymer melt by passing the polymer melt through at least one melt filter;
   c) transferring the purified polymer melt into at least one first reactor, wherein the purified polymer melt enters into a lower region (sump region) of the at least one first reactor at a temperature range of 220° C. to 300° C. and is conducted from the lower region (sump region) to an upper region (head region) of the at least one first reactor in a temperature gradient with heating to temperatures in a range of 330° C. to 360° C. such that a laminar melt flow is generated, wherein the polyolefins in the purified melt are cleaved into oligomers;
   d) transferring the oligomers formed in the at least one first reactor to at least one second reactor, wherein the oligomers introduced into the at least one second reactor have a temperature in the range of 330° C. to 360° C., and the oligomers are conducted in a temperature gradient in the at least one second reactor from a lower region (sump region) of the at least one second reactor to an upper region (head region) of the at least one second reactor with heating to 380° C. to 450° C., wherein the oligomers in the at least one second reactor are broken down to C3-C22 hydrocarbons in the presence of at least one clay mineral as a depolymerization catalyst, wherein the at least one first reactor and the at least one second reactor comprise a plurality of axial heating zones configured to generate the temperature gradient in the at least one first reactor and the temperature gradient in the at least one second reactor by stepwise heating;
   e) removing the C3-C22 hydrocarbons that are formed in the at least one second reactor to at least one precondenser, wherein the C3-C22 hydrocarbons exiting from the at least one second reactor are cooled in the at least one precondenser; and
   f) introducing the C3-C22 hydrocarbons that are cooled in the at least one precondenser into at least one main condenser, wherein the C3-C22 hydrocarbons exiting from the at least one precondenser are liquefied in the at least one main condenser.

2. The method as claimed in claim 1, wherein the polyolefins comprise a mixture of polyethylene and polypropylene.

3. The method as claimed in claim 1, wherein the polyolefins are melted in at least one extruder at temperatures of up to 300° C.

4. The method as claimed in claim 3, wherein a viscosity of the polymer melt at an exit of the at least one extruder is $1.0 \cdot 10^6$ to $2 \cdot 10^6$ mPas (300° C.).

5. The method as claimed in claim 1, wherein residual traces of impurities are removed from the polymer melt in the at least one melt filter.

6. The method as claimed in claim 1, wherein the purified polymer melt exiting from the at least one melt filter is introduced by at least one melt pump into the lower region (sump region) of the at least one first reactor, wherein the purified polymer melt, on entry into the at least one first reactor, has a viscosity from $1.0 \cdot 10^6$ to $2 \cdot 10^6$ mPas (300° C.).

7. The method as claimed in claim 1, wherein the polyolefins have a molecular weight of greater than $10^5$ kg/mol, and wherein the oligomers have a molecular weight between $10^2$ and $10^4$ kg/mol in the at least one first reactor.

8. The method as claimed in claim 1, wherein the oligomers leaving the upper region (head region) of the at least one first reactor have a viscosity between 500 and 1000 mPas (350° C.).

9. The method as claimed in claim 1, wherein the oligomers formed in the at least one first reactor are removed from the upper region (head region) of the at least one first reactor and introduced by at least one melt pump into the at least one second reactor.

10. The method as claimed in claim 1, wherein the oligomers leaving the at least one first reactor are mixed with the at least one clay mineral before they are introduced into the at least one second reactor.

11. The method as claimed in claim 1, wherein the at least one clay mineral comprises a layer silicate.

12. The method as claimed in claim 1, wherein the C3-C22 hydrocarbons are gaseous hydrocarbons.

13. The method as claimed in claim 1, wherein the C3-C22 hydrocarbons formed at the upper region (head region) of the at least one second reactor have a viscosity between 50 and 300 mPas (410° C.).

* * * * *